US008658196B2

(12) United States Patent
Janis (10) Patent No.: US 8,658,196 B2
(45) Date of Patent: Feb. 25, 2014

(54) GRAFT MATERIALS AND METHODS FOR STAGED DELIVERY OF BIOACTIVE COMPONENTS

(75) Inventor: Abram D. Janis, Valencia, CA (US)

(73) Assignee: Cook Biotech Incorporated, West Lafayette, IN (US)

(*) Notice: Subject to any disclaimer, the term of this patent is extended or adjusted under 35 U.S.C. 154(b) by 0 days.

(21) Appl. No.: 12/855,123

(22) Filed: Aug. 12, 2010

(65) Prior Publication Data

US 2010/0303886 A1 Dec. 2, 2010

Related U.S. Application Data

(63) Continuation of application No. PCT/US2008/087560, filed on Dec. 19, 2008.

(60) Provisional application No. 61/036,613, filed on Mar. 14, 2008.

(51) Int. Cl.
*A61F 2/00* (2006.01)
*A01N 37/18* (2006.01)
*A61K 38/00* (2006.01)
*A61P 31/04* (2006.01)
*A61K 38/18* (2006.01)
*C07K 14/475* (2006.01)
*C07K 14/49* (2006.01)
*C07K 14/495* (2006.01)
*C07K 14/50* (2006.01)
*C07K 14/485* (2006.01)
*A61P 29/00* (2006.01)

(52) U.S. Cl.
USPC .............. 424/423; 514/2.4; 514/7.6; 514/8.2; 514/8.9; 514/9.1; 514/9.6; 514/12.2

(58) Field of Classification Search
None
See application file for complete search history.

(56) References Cited

U.S. PATENT DOCUMENTS

| 3,562,820 | A | 2/1971 | Braun |
| 2003/0039695 | A1* | 2/2003 | Geistlich et al. .............. 424/484 |
| 2005/0021141 | A1* | 1/2005 | Bleyer et al. ................ 623/15.12 |
| 2006/0201996 | A1* | 9/2006 | Hodde ........................... 228/101 |
| 2007/0004961 | A1* | 1/2007 | Case et al. ....................... 600/37 |
| 2007/0184122 | A1 | 8/2007 | Johnson |

FOREIGN PATENT DOCUMENTS

| EP | 1283063 A1 | 2/2003 |
| WO | WO 98/49969 A1 | 11/1998 |
| WO | WO 03/035125 A2 | 5/2003 |

OTHER PUBLICATIONS

Richardson, Thomas P., Peters, Martin C., Ennett, Allessandra B., Mooney, David J., Polymeric System for Dual Growth Factor Delivery, Natur Biotechnology, vol. 19, Nov. 2001, pp. 1029-1034.
Wang, Jian Fei, Olson, Merle E., Reno, Carylyn R., Kulyk, William, Wright, J. Barry, Hart, David A., Molecular and Cell Biology of Skin Wound Healing in a Pig Model, Connective Tissue Resarch, vol. 41(3), pp. 195-211, Jan. 20, 2000.

* cited by examiner

*Primary Examiner* — Chris R Tate
*Assistant Examiner* — Douglas F White
(74) *Attorney, Agent, or Firm* — Woodard, Emhardt, Moriarty, McNett & Henry LLP (57) ABSTRACT

Described, in certain aspects of the invention, are multilaminate medical graft products, as well as methods for preparing and using the same. An illustrative multilaminate medical graft product of the invention comprises a first layer of remodelable extracellular matrix (ECM) material bonded to a second layer of remodelable ECM material, wherein the first material layer is enriched with a growth factor relative to the second material layer. Such a remodelable ECM material may be comprised of submucosa from a warm-blooded vertebrate, for example, porcine small intestinal submucosa (SIS).

21 Claims, 2 Drawing Sheets

GRAFT MATERIALS AND METHODS FOR STAGED DELIVERY OF BIOACTIVE COMPONENTS

REFERENCE TO RELATED APPLICATIONS

The present application is a continuation application of PCT Patent Application Serial No. PCT/US2008/087560 filed Dec. 19, 2008 entitled GRAFT MATERIALS AND METHODS FOR STAGED DELIVERY OF BIOACTIVE COMPONENTS, which was published in English under Article 21(2) and which claims the benefit of U.S. Provisional Patent Application Ser. No. 61/036,613, filed Mar. 14, 2008, abandoned, entitled GRAFT MATERIALS AND METHODS FOR STAGED DELIVERY OF BIOACTIVE COMPONENTS, both of which are incorporated by reference herein in their entirety.

BACKGROUND

The present invention relates generally to medical devices and in particular aspects to tissue graft devices that are comprised of extracellular matrix material layers having properties that differ from one another.

As further background, when tissue is damaged or otherwise disrupted, whether by disease, by trauma including surgery, or in any other manner, a series of interdependent physiological events occur that result in tissue repair. These events occur within (or are otherwise associated with) what are generally believed to be the four major phases of healing: inflammation, cell proliferation, matrix deposition, and remodeling. Tissue wound healing is a dynamic, complex process that involves the integrated action of several body components such as but not limited to extracellular matrix materials, various cell types, and soluble mediators (i.e., cytokines and growth factors).

Dermal wound healing is especially critical to maintaining the body's primary line of defense. The skin provides the body with a protective barrier from, among other things, chemical and mechanical challenges, harmful pathogens, and ultraviolet radiation. Chronic wounds compromise the skin's ability to defend against these agents, due to the prolonged wound healing process. For chronic wounds, the body is unable to complete the wound healing process due to a compromised vascular and/or immune system. Without clinical intervention, these chronic wounds can lead to the spread of infection, significant necrotic tissue, and other bodily problems including possible amputation in the case of ulcers in the foot. Advanced states of chronic dermal wounds present a significant clinical challenge. In the United States alone, there are over 3 million cases of chronic wounds annually.

A variety of medical graft products have been developed for treating cutaneous, intracutaneous, and subcutaneous tissues. Likewise, a variety of materials have been used to form these products, including collagenous materials. Suitable collagenous materials can be provided by collagenous extracellular matrix (ECM) materials. Such ECM materials can be provided, for example, by materials isolated from a suitable tissue source from a warm-blooded vertebrate, e.g., from the submucosal tissue of a mammal. Such isolated submucosal tissue, for example, small intestinal submucosa (SIS), can be processed so as to have bioremodelable properties and promote cellular invasion and ingrowth. Illustratively, sheet-form SIS material has been used as a surgical graft to provide tissue support in patients, e.g., in hernia repair operations. In some forms, the sheet-form SIS material includes a multilayered configuration to provide strength, reinforcement, and/or other enhancements to the graft.

There remain needs for improved and/or alternative tissue graft devices, as well as methods for forming and utilizing the same. The present invention is addressed to those needs.

SUMMARY

The present invention provides, in certain aspects, unique multilayered medical graft products that include material layers having bioactive properties that differ from one another. Illustratively, certain embodiments of the present invention relate to multilaminate graft materials that include first and second layers of material that differ from one another relative to their incorporation or degree of incorporation of one or more bioactive components such as one or more growth factors. For example, one inventive multilaminate medical graft product includes a first layer of remodelable extracellular matrix (ECM) material bonded to a second layer of remodelable ECM material, wherein the first material layer is enriched with transforming growth factor beta (TGF-beta) relative to the second material layer. In this regard, the first material layer has the capacity to facilitate and/or promote the repair of damaged tissue differently than the second material layer, and the multilaminate graft product as a whole has the capacity to provide differential treatment to a wound site as it remodels. Other suitable growth factors useful in the invention include but are not limited to basic fibroblast growth factor (FGF-2), epidermal growth factor (EGF), platelet derived growth factor (PDGF), and cartilage derived growth factor (CDGF). In some forms of the invention, one or more layers of a multilaminate graft product comprise submucosa, e.g., porcine small intestinal submucosa (SIS).

In one embodiment, the invention provides a method of preparing a multilaminate medical graft product. This method comprises the steps of: (i) providing first and second layers of remodelable ECM material; (ii) enriching the first remodelable ECM material layer with a growth factor relative to the second remodelable ECM material layer; (iii) and bonding the first and second layers of remodelable ECM material to one another. Such an enriching step may occur before or after the first and second layers of material are bonded together, and may include the addition of one or more growth factors to the first material layer and/or the removal of one or more growth factors from the second material layer. Also, the material layers may be bonded to one another in any suitable manner including but not limited to by vacuum pressing and/or using an adhesive.

Another embodiment of the present invention provides a medical product which comprises a multilaminate medical graft product such as that described above enclosed within a sealed package. In certain forms, such a medical product includes a plurality of multilaminate graft products, wherein each product may or may not exhibit the same general size and shape. Further, this sealed package can be configured to maintain the multilaminate medical graft product in a sterile condition when the product is packaged therein, and in one aspect, the package includes indicia to communicate information about its contents.

One aspect of the invention provides a method of tissue grafting. This method comprises applying to tissue of a patient a multilaminate medical graft product such as that described above. In certain embodiments, such a method comprises applying an inventive multilaminate product to a wound site that includes cutaneous, subcutaneous, and/or intracutaneous tissue.

An additional aspect of the invention provides a method of treating an open cutaneous wound. This method comprises applying to the wound a multilaminate medical graft product such as that described above. In some forms, such a method comprises applying a meshed multilaminate product to an open cutaneous wound, e.g., an ulcer or a burn to the skin.

In another embodiment, the invention provides a method of forming a medical graft product which comprises providing a medical graft material comprising at least a first layer of remodelable extracellular matrix material and a second layer of remodelable extracellular matrix material, and enriching the first layer of extracellular matrix material with a bioactive component (e.g., a growth factor) relative to the second layer of extracellular matrix material.

Other objects, embodiments, forms, features, advantages, aspects, and benefits of the present invention shall become apparent from the detailed description and drawings included herein.

DETAILED DESCRIPTION

While the present invention may be embodied in many different forms, for the purpose of promoting an understanding of the principles of the present invention, reference will now be made to the embodiments illustrated in the drawings, and specific language will be used to describe the same. It will nevertheless be understood that no limitation of the scope of the invention is thereby intended. Any alterations and further modifications in the described embodiments and any further applications of the principles of the present invention as described herein are contemplated as would normally occur to one skilled in the art to which the invention relates.

As disclosed above, in certain aspects, the present invention provides unique multilaminate medical graft products that include first and second bonded layers of material that differ from one another relative to their incorporation or extent of incorporation of one or more bioactive components. For example, a preferred multilaminate medical graft product includes a first layer of remodelable extracellular matrix (ECM) material bonded to a second layer of remodelable ECM material, wherein the first material layer is enriched with a growth factor relative to the second material layer. The invention also provides grafting methods utilizing such multilaminate medical graft products. Particularly advantageous methods involve the treatment of damaged tissue, for example, the treatment of externally exposed tissue wounds such as burn wounds to the skin, or internal wounds such as surgically repaired tissue. The invention also provides methods of manufacturing such multilaminate constructs and medical products that include such constructs enclosed within sterile packaging.

Figure 1:
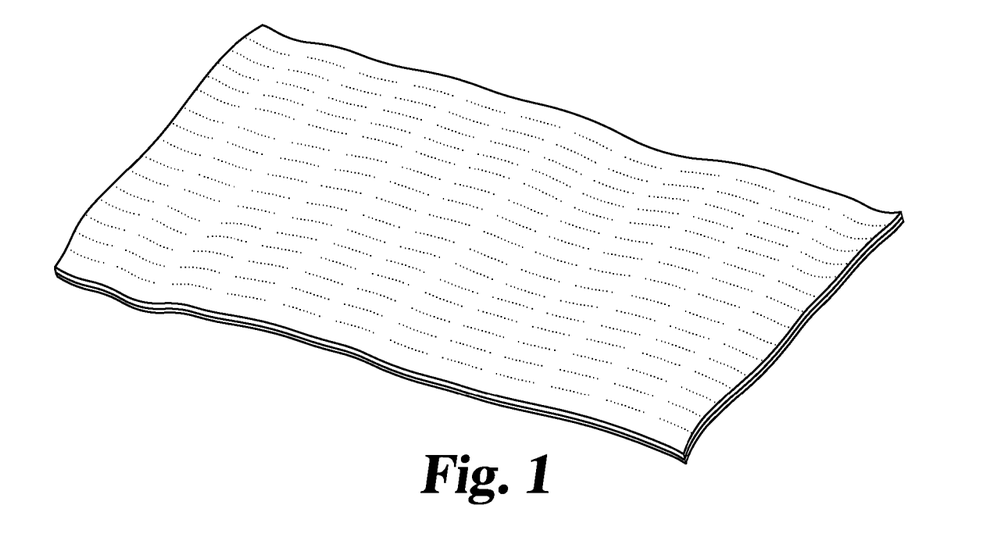
FIG. 1 is a perspective view of medical graft product of the present invention.

With reference now to FIG. 1, shown is an illustrative medical graft device 20 of the present invention. The graft device 20 includes a first layer of ECM material 21 bonded to a second layer of ECM material 22, wherein the first ECM layer 21 is enriched with a particular growth factor relative to the second ECM layer 22. In certain embodiments, at least a portion of this growth factor component is exogenous to the ECM material source.

This difference between layers allows the graft device 20 to facilitate and/or promote the repair of damaged tissue differentially as it remodels. Illustratively, the device 20 can be applied to a tissue wound with the first layer-side of the device facing the wound, so that the first layer 21 begins the remodeling process before the second layer 22. In this regard, the device as a whole has the capacity to deliver relatively more of the growth factor to the wound site during early stages of the healing process and relatively less of the growth factor to the wound site during later stages of the healing process.

Turning now to a more detailed discussion of materials useful in forming devices of the invention, these materials should generally be biocompatible, and in advantageous embodiments of the devices, are comprised of a remodelable material. Particular advantage can be provided by devices including a remodelable collagenous material. Such remodelable collagenous materials, whether reconstituted or naturally-derived, can be provided, for example, by collagenous materials isolated from a warm-blooded vertebrate, and especially a mammal. Such isolated collagenous material can be processed so as to have remodelable, angiogenic properties and promote cellular invasion and ingrowth. Remodelable materials may be used in this context to promote cellular growth on, around, and/or within tissue in which a device of the invention is implanted.

Suitable remodelable materials can be provided by collagenous extracellular matrix (ECM) materials possessing biotropic properties. For example, suitable collagenous materials include ECM materials such as those comprising submucosa, renal capsule membrane, dermal collagen, dura mater, pericardium, fascia lata, serosa, peritoneum or basement membrane layers, including liver basement membrane. Suitable submucosa materials for these purposes include, for instance, intestinal submucosa including small intestinal submucosa, stomach submucosa, urinary bladder submucosa, and uterine submucosa. Collagenous matrices comprising submucosa (potentially along with other associated tissues) useful in the present invention can be obtained by harvesting such tissue sources and delaminating the submucosa-containing matrix from smooth muscle layers, mucosal layers, and/or other layers occurring in the tissue source. For additional information as to some of the materials useful in the present invention, and their isolation and treatment, reference can be made, for example, to U.S. Pat. Nos. 4,902,508, 5,554,389, 5,993,844, 6,206,931, and 6,099,567.

Submucosa-containing or other ECM tissue used in the invention is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 may be characteristic of any ECM tissue used in the present invention.

A typical layer thickness for an as-isolated submucosa or other ECM tissue layer used in the invention ranges from about 50 to about 250 microns when fully hydrated, more typically from about 50 to about 200 microns when fully hydrated. These layer thicknesses may vary with the type and age of the animal used as the tissue source. As well, these layer thicknesses may vary with the source of the tissue obtained from the animal source. In some forms, multilaminate graft devices of the invention are constructed so as to provide an overall device thickness of at least about 150 microns, typically ranging from about 150 to about 1000 microns, and in certain embodiments ranging from about 200 to about 1000 microns. Such relatively thick constructs can provide advantageous and lasting ECM material scaffolds for tissue ingrowth, especially in the field of wound care such as burn and ulcer care. In addition to such thicknesses, typical graft products of the invention in sheet-form can have lengths and widths ranging from about 2 cm to about 50 cm.

Submucosa or other ECM materials of the present invention can be derived from any suitable organ or other tissue source, usually sources containing connective tissues. The ECM materials processed for use in the invention will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multi-axial but regularly oriented fibers. When processed to retain native bioactive factors, the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination with appropriate staining. Such non-collagenous solids can constitute a significant percentage of the dry weight of the ECM material in certain inventive embodiments, for example at least about 1%, at least about 3%, and at least about 5% by weight in various embodiments of the invention.

The submucosa or other ECM material used in the present invention may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the formation of new blood vessels into the materials. Methods for measuring in vivo angiogenesis in response to biomaterial implantation have recently been developed. For example, one such method uses a subcutaneous implant model to determine the angiogenic character of a material. See, C. Heeschen et al., Nature Medicine 7 (2001), No. 7, 833-839. When combined with a fluorescence microangiography technique, this model can provide both quantitative and qualitative measures of angiogenesis into biomaterials. C. Johnson et al., Circulation Research 94 (2004), No. 2, 262-268.

Continuing with FIG. 1 (and as described above), the first material layer 21 is enriched with a growth factor relative to the second material layer 22. In this context, "enriched" means that the first material layer 21 is more concentrated in this particular growth factor than the second material layer 22. Illustratively, in some embodiments, the first material layer 21 contains a certain amount of TGF-beta, while the second material layer 22 contains essentially none. In other embodiments, the first and second material layers 21 and 22 both include TGF-beta; however, the TGF-beta concentration provided by the first material layer 21 is sufficient to affect the wound site differently than the TGF-beta concentration provided by the second material layer 22 as the two layers remodel. In such embodiments, the growth factor enrichment of the first material layer 21 relative to the second material layer 22 can be varied, for example, to suit a particular treatment application. Further, enriching the first layer 21 with a particular growth factor relative to the second layer 22 can mean adding this growth factor to the first material layer 21 and/or removing this growth factor from the second material layer 22. Also, the concentration of a particular growth factor within a material layer may include native and/or non-native forms of the growth factor. For example, a material layer could include both exogenous and endogenous TGF-beta.

In certain embodiments, a multilayered graft product includes at least two layers of ECM material, wherein a first ECM material layer contains or otherwise carries at least 10% more of a particular bioactive component (e.g., a growth factor) on a weight to weight basis than a second ECM material layer. In some forms, a first ECM material layer contains at least 20% more of a particular bioactive component (e.g., a growth factor) on a weight to weight basis than a second ECM material layer in such a product.

Suitable ECM materials may retain one or more bioactive components native to the source of the ECM material. These bioactive substances can include but are not limited to proteins, glycoproteins, proteoglycans, and glycosaminoglycans. For example, an ECM material may retain heparin, heparin sulfate, hyaluronic acid, fibronectin, cytokines, and the like. As well, a collagenous ECM material may retain one or more growth factors such as but not limited to basic fibroblast growth factor (FGF-2), transforming growth factor beta (TGF-beta), epidermal growth factor (EGF), platelet derived growth factor (PDGF), and/or cartilage derived growth factor (CDGF). Thus, generally speaking, a submucosa or other ECM material may retain one or more bioactive components that induce, directly or indirectly, a cellular response such as a change in cell morphology, proliferation, growth, or protein or gene expression.

Accordingly, certain graft products of the invention can include a first layer of ECM material having a given percentage or level of one or more growth factors, particularly FGF-2, relative to a second layer of ECM material in the product. For example, in some forms, an inventive graft product comprises: (i) a first layer of ECM material containing FGF-2 at a level of at least about 50 nanograms per gram dry weight; and (ii) a second layer of ECM material containing a considerably lower amount of FGF-2, e.g., no more than about 40 ng/g dry weight, no more than about 20 ng/g dry weight, no more than about 10 ng/g dry weight, or essentially free of FGF-2. In other forms, inventive products comprise a first layer of ECM material containing FGF-2 at a level of at least about 60, at least about 70, at least about 80, or at least about 100 ng/g dry weight, and further comprise a second layer of ECM material containing a considerably lower amount of FGF-2 relative to the first ECM material layer in the given product. Illustratively, such a product can include a first ECM material layer containing FGF-2 at a level of at least about 85 ng/g dry weight and a second ECM material layer containing FGF-2 at a level of no more than 55 ng/g dry weight. In other embodiments of the invention, a first ECM layer in a product has a suitable level of a bioactive component, such as FGF-2 or another growth factor, and second ECM layer in that same product has at least about 10% less of the FGF-2 or other bioactive component than the first ECM layer, or at least about 15%, at least about 25%, at least about 50%, or at least about 75% less of the FGF-2 or other bioactive component than the first ECM layer.

Further, in addition or as an alternative to the inclusion of such native bioactive components, non-native bioactive components such as those synthetically produced by recombinant technology or other methods (e.g., genetic material such as DNA), may be incorporated into a layer of remodelable ECM material of the invention. These non-native bioactive components may be naturally-derived or recombinantly produced proteins that correspond to those natively occurring in an ECM tissue, but perhaps of a different species (e.g., human proteins applied to collagenous ECMs from other animals, such as pigs). The non-native bioactive components may also be drug substances. Illustrative drug substances that may be added to material layers include, for example, anti-clotting agents (e.g., heparin), antibiotics, anti-inflammatory agents, therapeutic proteins, and anti-proliferative agents (e.g., taxol derivatives such as paclitaxel). Such non-native bioactive components can be incorporated into and/or onto material layers of the invention in any suitable manner, for example, by surface treatment (e.g., spraying) and/or impregnation (e.g., soaking).

The multilaminate medical graft products of the invention can include any suitable number of layers of remodelable ECM material bonded to one another. Preferred such products include from about 2 to about 40 material layers, more typically from about 2 to about 10 material layers. Illustratively, one or more additional layers of remodelable ECM material, e.g., one, two, three, four, five, six, seven, eight, or more additional layers of ECM material, can be bonded to the graft device 20 depicted in FIG. 1. For example, one or more additional layers of remodelable submucosa can be stacked above, below, and/or between the first material layer 21 and the second material layer 22. Also, any of such additional layers can resemble the first material layer 21 or the second material layer 22 with regard to its incorporation or degree of incorporation of one or more growth factors or other bioactive components. As one example, a multilaminate graft product can comprise six layers of porcine small intestinal submucosa (SIS) bonded to one another, wherein one half of the product (i.e., a first three layers) is enriched in an anti-inflammatory agent relative to the other half of the product (i.e., a second three layers).

Similarly, the multilaminate medical graft products of the present invention are not limited to the inclusion of a single bioactive component. To the contrary, any material layer utilized in the invention can incorporate any number of different bioactive components (again, whether or not exogenous or endogenous to the tissue source). Illustratively, one or more additional growth factors or other bioactive components (e.g., cytokines) can be included in the first material layer 21 and/or the second material layer 22 of the graft device 20 of FIG. 1 (and/or any additional material layer(s) that might be added as described above). In this regard, in certain aspects of the invention, one or more bioactive components will be distributed among the material layers of a graft device in any suitable manner and such that at least one layer is enriched with at least one bioactive component relative to at least one other layer. As just one example, a two-layer graft device can incorporate three different growth factors such that the material layers contain approximately equal concentrations of two of the growth factors, but one of the material layers is enriched in the remaining growth factor relative to the other material layer.

Graft devices of the invention find wide use in the field of medicine, and in this regard, can be adapted to provide a variety of devices and objects suitable for application to and/or implantation within a patient. The present invention also provides, in certain aspects, various methods for using these materials, for example, to replace, augment, repair, and/or otherwise suitably treat diseased or otherwise damaged or defective tissue of a patient. Illustratively, grafting materials of the invention can be configured as implantable devices suitable for tissue grafting, bulking tissue, providing hemostasis, and/or providing occlusion in a passageway or other open space within the body of a patient (e.g., as an embolization device, fistula plug, etc.). In some embodiments, grafting products of the invention are configured as single- or multi-layered patches or other sheet or sheet-like devices for providing support to patient tissue or otherwise treating patient tissue. Illustratively, inventive graft materials can provide wound healing products suitable for cutaneous, intracutaneous, and/or subcutaneous wound treatment, e.g., a hernia repair patch or a burn treatment material. As well, sheet-form graft products of the invention find use as precursor materials for forming a variety of other medical devices, or components thereof. Illustratively, graft materials of the invention can be processed into various shapes and configurations, for example, into a urethral sling or a prosthetic body part. In some forms, sheet-form graft materials of the invention are suitable for forming tubular grafting devices, which may be used to replace a circulation vessel, or a portion thereof, or to bypass a blocked vessel.

In certain embodiments, the graft device 20 is applied to an open cutaneous wound. Open, cutaneous wounds may be classified into one of four grades depending on the depth of the wound. A Grade I wound is limited to the epithelium. A Grade II wound extends into the dermis. A Grade III wound extends into the subcutaneous tissue; and, a Grade IV wound (or full-thickness wound) exposes bone. The term "partial thickness wound" refers to wounds that encompass Grades I-III; examples of partial thickness wounds include burn wounds, pressure sores, venous stasis ulcers, and diabetic ulcers. Advantageous applications of products of the invention include the treatment of partial thickness open cutaneous wounds, including burns and ulcers. These wounds are often chronic (e.g. lasting at least about 30 days untreated), and benefit significantly from the application of graft products of the present invention.

In use for cutaneous wound care, the physician, veterinarian or other user of the medical graft materials of the invention can prepare the wound for treatment in a conventional fashion, which may for example include cleaning and/or debridement of the wound with water, physiologic saline or other solutions, and potentially also treating the wound with antibiotics or other therapeutic agents. The medical graft construct of the invention can then be applied to the wound in a fashion to facilitate and promote healing of the wound. In this regard, the inventive construct may be applied in a dehydrated or hydrated state. Once applied to a wound, this ECM construct will hydrate (if not previously hydrated) and remain generally in place either alone or in combination with other wound dressing materials applied below or on top of the ECM material graft product.

In certain embodiments, it may be advantageous for one or more layers of the multilaminate product to be processed so as to exhibit a meshed structure (as shown in phantom in FIG. 1). Such a meshed structure will have a plurality of slits therein to provide a mesh pattern, and the mesh pattern will provide deformability to the structure, especially expandability. In this regard, in the preferred meshed constructs, expansion or other deformation of the structure will widen the openings created by the slits of the mesh pattern, by lateral and/or vertical displacement of the edges of the slits relative to one another. Preferred meshed devices of the invention will have a mesh pattern providing an expansion ratio of at least about 1.2:1 when the layer is completely hydrated, more preferably at least about 2:1, and most preferably at least about 3:1. Such highly deformable structures provide surprisingly beneficial properties to the graft product, particularly in the field of wound care.

A meshed pattern can be created using suitable meshing devices designed for processing skin autograft sections. Such devices typically include a cylindrical drum cutter with a plurality of edges for providing the slit pattern of the mesh. A variety of such devices are known and can be used in the invention. For additional information as to meshers, reference may be made to U.S. Pat. Nos. 5,004,468, 6,063,094, 3,472,228, 3,358,688, and 3,640,279. These and other devices incorporating a meshing drum provide for a convenient, high-through put method of preparing meshed material layers or graft devices of the invention. It will be understood, however, that the mesh pattern can be made by hand-cutting the material or by using appropriate cutting tools with multiple blades to cut the slits to provide the mesh pattern.

As previously mentioned, in certain aspects of the invention, one or more growth factors will be distributed among the material layers of a graft device (in any suitable manner and in any suitable concentration) such that at least one layer is enriched with at least one growth factor relative to at least one other layer. Accordingly, certain aspects of the invention provide multilaminate graft devices including a plurality of growth factors, wherein the distribution of the growth factors among the material layers and the concentrations of the various growth factors within the layers are selected so as to optimally promote and/or facilitate the healing process, for example, by delivering certain amounts of certain growth factors at certain times during the remodeling of the graft device.

In some aspects, the graft device provides more than one bioactive component for delivery to a treatment site. For example, in certain embodiments, a graft device includes a first layer of remodelable ECM material bonded or otherwise adjoined to a second layer of remodelable ECM material, wherein the first material layer is enriched with a first bioactive component (e.g., a growth factor) relative to the second material layer, and the second material layer is enriched with a second bioactive component (e.g., a growth factor) relative to the first material layer. In these embodiments, the first bioactive component may be selected based on its effectiveness in promoting and/or facilitating earlier phases of a healing or other treatment process, and the second bioactive component may be selected based on its effectiveness in promoting and/or facilitating later phases of this process. Accordingly, the graft device can be applied to a wound site (e.g., an open cutaneous wound) so that the first material layer begins the remodeling process before the second material layer. In this regard, as the graft device as a whole remodels, it has the capacity to deliver relatively more of the first bioactive component to the wound during the early stages of remodeling process and relatively more of the second bioactive component to the wound site during later stages of the remodeling process.

In particular, one multilaminate tissue graft embodiment includes a first ECM layer that is enriched in VEGF relative to a second ECM layer, wherein the second ECM layer is enriched in PDGF relative to the first ECM layer. Another multilaminate tissue graft embodiment includes a first ECM layer that is enriched in an anti-inflammatory agent relative to a second and third ECM layer, wherein the second ECM layer is enriched in a growth factor optimal for promoting granulation tissue formation relative to the first and third ECM layers, and wherein the third ECM layer is enriched in a growth factor optimal for promoting angiogenesis relative to the first and second ECM layers.

In certain embodiments, a wound healing product includes two or more multilaminate graft products (e.g., pads, patches, bandages, etc.), wherein each graft product is optimized for a different phase of a healing process. Such wound healing products are particularly useful for treating dermal wounds, for example chronic wounds such as chronic ulcers, that are readily accessible for multiple applications.

As mentioned above, the graft devices of the invention can be adapted for internal body applications as well. For example, in certain embodiments, the graft device of FIG. 1 is applied to an internal wound site in such a way that the first material layer-side of the device 20 contacts the wound site directly, and the second material layer-side of the device 20 faces away from the wound site (i.e., is exposed to other body parts within the patient). In these embodiments, the first and second material layers 21 and 22 will generally be infiltrated by the patient's native cells at or near the same time. However, because of the spatial orientation of the layers in relation to the wound, as the device 20 remodels, the wound can receive more of the growth factor during early stages of the healing process and less of the growth factor during later stages of the healing process. Further, a graft device of the invention can be applied to any internal wound site. For example, in certain aspects, a graft device of the invention is applied to ulcerated internal tissue such as but not limited to an ulcerated blood vessel. In other aspects, such a device is applied to surgically repaired tissue such as but not limited to a hernia.

Multilaminate graft products of the present invention can have any suitable size, shape, and/or configuration. For example, a multilaminate graft product of the invention can be in the shape of a bead. Illustratively, a multilayered bead can have a first ECM material layer (e.g., a core) and a second ECM material layer (e.g., a cover), wherein the first layer is enriched in a bioactive substance relative to the second layer. Such a bead product can be part of a liquid or solid matrix. In certain forms, a gel comprising such multilayered beads is injected into a patient as a method of treatment, for example, as an embolic device to treat an aneurysm.

Embodiments of the invention also encompass methods of manufacturing graft product such as device 20. Illustratively, one method comprises the steps of: (1) enriching a first ECM material layer with a growth factor relative to a second ECM material layer; and (2) bonding the first ECM material layer to the second ECM material layer. In such method embodiments, the bonding step may occur before or after the enriching step. Similarly, when any additional growth factors or other bioactive components are incorporated into the first ECM material layer, the second ECM material layer, and/or any additional material layer(s), such incorporation may occur before or after any bonding step (i.e., after all of the layers are bonded together or after any two layers are bonded together).

Any suitable bonding technique can be used in the present invention to bond two or more layers of material together. For example, in certain embodiments, a dehydration bond is formed between layers of material, for example, by subjecting the material layers to drying and compressing conditions. Illustratively, the material layers, or any portions thereof, can be compressed together and allowed to dry by evaporation (e.g., air dry). Such evaporative drying can be enhanced in a number of ways, such as by blowing air over the compressed material layers, by increasing the temperature of the compressed material layers, or by any other suitable means or any suitable combination thereof. Material layers utilized in the invention may also be held together or otherwise combined in a variety of fashions. These include but are not limited to using an adhesive, suturing, using mechanical fastener(s), and/or any other suitable joining means. Illustratively, two device layers may be held together by an absorbable substance or device (e.g., a 2-0 vicryl suture material), which can then degrade some time after implantation. Other effective ways to assemble two or more device parts will be recognized by those skilled in the art, and therefore, are encompassed by the present invention.

The first material layer and the second material layer are desirably of a character so as to form an attachment to one another by virtue of being dried while compressed against each other. For example, the material layers can each include a collagenous material, especially a collagenous extracellular matrix material. Dehydration of the collagenous materials in forced contact with one another effectively bonds the materials to one another, even in the absence of other agents for achieving a bond, although such agents can be used while also taking advantage at least in part on the dehydration-induced bonding. With sufficient compression and dehydration, the two collagenous materials can be caused to form a generally unitary collagenous structure with each layer substantially retaining whatever bioactive makeup it possessed before the bonding step occurred. Vacuum pressing operations, and the closely bonded nature that they can characteristically impart to the layers of material, are highly advantageous and preferred in these aspects of the invention.

In this regard, suitable equipment for use for vacuum pressing in the present invention can be commercially obtained. One such vacuum pressing apparatus is commercially available from Zip-Vac East, Incorporated, Kennesaw, Ga. This vacuum pressing apparatus has a flexible chamber that has a vacuum drawn on it, which pulls the flexible boundaries of the chamber onto and around the article in the chamber. The vacuum also removes water from hydrated materials within the chamber.

During any bonding operation of the invention that involves compressing two or more material layers together to form a multilaminate construct (e.g., a vacuum pressing operation, etc.), it should be noted that the material layers can be compressed in any suitable manner including but not limited to placing the material layers, or any portions thereof, in a press, between rollers, and the like. Also, the material layers, or any portions thereof, may be compressed at any time during a bonding operation.

Although not necessary, in preferred aspects, a multilaminate construct in accordance with the present invention comprises a plurality of similarly-sized sheets of remodelable ECM material bonded together, wherein the sheets substantially overlap one another. In such aspects, at least one region of the multilaminate construct can be compressed differently than at least one other region of the multilaminate construct. Illustratively, a peripheral region of the multilaminate construct can be compressed with a certain amount of pressure, while an inner region of the construct can be compressed with relatively less pressure (or no pressure), or vice versa. Alternatively, certain regions of the construct can be compressed so as to form a particular pattern, e.g., repeating geometrical shapes of the same size or different sizes, across the top and/or bottom surface of the construct, or any portions thereof, wherein other regions of the construct are compressed with relatively less pressure or no pressure at all.

In one embodiment, the porosity of a layer of remodelable ECM material is lowered by drying the material under compression. In general, compressing a pliable open matrix material, such as a pliable ECM material, increases the material's bulk density and decreases the material's porosity by decreasing the size of the voids in the open matrix. As is the case in certain aspects of the invention, when such a material is dried while being compressed, particularly under vacuum pressing conditions, the open matrix structure can become generally fixed in this relatively higher bulk density, lower porosity state (i.e., in a relatively more collapsed state). It should be noted that different compressing and drying techniques and/or methods, including different degrees of compressing and drying, can be designed through routine experimentation so as to allow for a material layer having an optimal degree of material bulk density and/or porosity for a particular graft material formation method.

A layer of material of the invention can have a level of porosity. Accordingly, a multilaminate product of the invention can have layers with differing porosities. For example, the graft device 20 can be configured so that the first material layer 21 has a different porosity than the second material layer 22. Remodelable ECM materials having a relatively more open matrix structure (i.e., higher porosity) are capable of exhibiting different material properties than those having a relatively more closed or collapsed matrix structure. For example, an ECM material having a relatively more open matrix structure is generally softer and more readily compliant to an implant site than one having a relatively more closed matrix structure. Also, the rate and amount of tissue growth in and/or around a remodelable material can be influenced by a number of factors, including the amount of open space available in the material's matrix structure for the infusion and support of a patient's cell building components, such as fibroblasts. Therefore, a more open matrix structure can provide for quicker, and potentially more, growth of patient tissue in and/or around the remodelable material, which in turn, can lead to quicker remodeling of the material by patient tissue. Accordingly, a more open matrix structure can provide for quicker release of any bioactive components contained therein.

Certain method embodiments of the invention include subjecting one or more layers of material, or portions thereof, to lyophilization conditions. For example, in certain embodiments, a multilaminate product is lyophilized before placing it in packaging for storage. In other embodiments, lyophilization is part of a bonding step, for example, part of dehydration bonding one or more ECM material layers together. Such lyophilization can include freeze-drying the material, for example, freezing the material, including any hydrate contained therein, and thereafter placing the material under vacuum. When sufficient vacuum is applied, as is known in the art, the frozen hydrate will generally sublime, i.e., turn directly from a solid to a gas. The resulting water vapor can then be removed from the material, thereby drying the material. Alternatively, subjecting one or more layers of material to lyophilization conditions can include, in certain aspects, applying sufficient vacuum to the material to cause evaporative cooling, which simultaneously freezes and dries the material. Utilizing evaporative cooling can eliminate having to "pre-freeze" the material.

As previously mentioned, certain aspects of the invention provide a method of forming a multilayered graft material, wherein the material layers are sufficiently bonded together (e.g., dehydrothermally bonded) by subjecting them to drying and compressing conditions. Nonetheless, it should be noted that other aspects of the invention provide methods of forming multilayered graft materials, wherein an adhesive, glue, adherent polymer or other bonding agent is used to help form or augment such a material bond. Suitable bonding agents may include, for example, collagen gels, gelatin, fibrin glue, or other agents including reactive monomers or polymers, for example cyanoacrylate adhesives.

ECM materials used in the invention may be free of additional, non-native crosslinking, or may contain additional crosslinking. Such additional crosslinking may be achieved by any suitable means including but not limited to by photocrosslinking techniques, by chemical crosslinkers, or by protein crosslinking induced by dehydration or other means. When additionally crosslinked, remodelable ECM material of the invention can be additionally crosslinked internally within a single layer, and/or crosslinking may be used in whole or in part to bond multiple ECM material layers to one another. Further, individual material layers within a multi-layer construct may be subjected to crosslinking conditions prior to bonding them together, while bonding them together, and/or after bonding them together. Nonetheless, because certain crosslinking techniques, certain crosslinking agents, and/or certain degrees of crosslinking can destroy the remodelable properties of a remodelable material, where preservation of remodelable properties is desired, any crosslinking of the remodelable ECM material can be performed to an extent or in a fashion that allows the material to retain at least a portion of its remodelable properties.

Chemical crosslinkers that may be used include, for example, aldehydes such as glutaraldehydes, diimides such as carbodiimides, e.g., 1-ethyl-3-(3-dimethylaminopropyl) carbodiimide hydrochloride, ribose or other sugars, acyl-azide, sulfo-N-hydroxysuccinamide, or polyepoxide compounds, including for example polyglycidyl ethers such as ethyleneglycol diglycidyl ether, available under the trade name DENACOL EX810 from Nagese Chemical Co., Osaka, Japan, and glycerol polyglycerol ether available under the trade name DENACOL EX 313 also from Nagese Chemical Co. Typically, when used, polyglycerol ethers or other polyepoxide compounds will have from 2 to about 10 epoxide groups per molecule.

The present invention also provides a line of medical products, wherein such medical products can include one or more tissue graft devices such as those disclosed herein enclosed within a sealed package. When these medical products include more than one graft device, for example, a plurality of graft devices, the devices can each be of substantially the same size and shape, or, alternatively, can vary with respect to size and shape.

Figure 2:
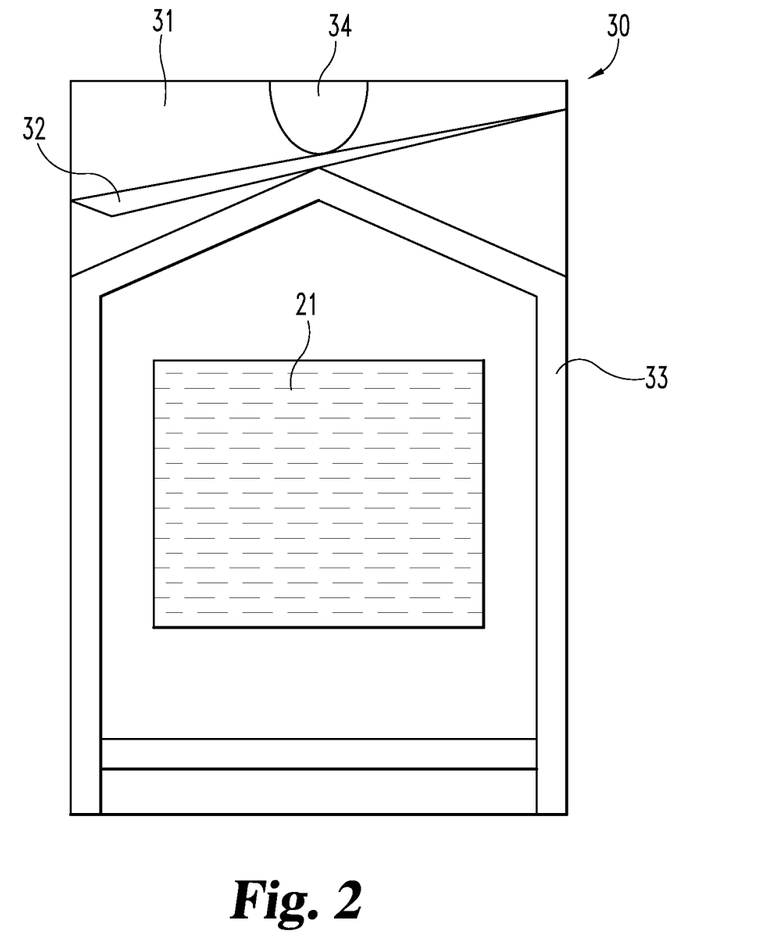
FIG. 2 is a top view of a medical product of the present invention.

With reference now to FIG. 2, shown is a top view of an illustrative medical product 30 of the present invention that includes tissue graft device 20 sealed within sterile medical packaging. In particular, medical product 30 has packaging including a backing layer 31 and a front film layer 32 (shown partially drawn away from backing layer 31). The graft device is sealed between backing layer 31 and film 32 utilizing a boundary of pressure-adhesive 33 as is conventional in medical packaging. A cut-out 34 may be provided in the backing layer 31 to assist a user in separating the film layer 32 from the backing layer 31.

Sterilization of the medical product 30 may be achieved, for example, by irradiation, ethylene oxide gas, or any other suitable sterilization technique, and the materials and other properties of the medical packaging will be selected accordingly. Also, tissue graft devices of the invention can be contained in a sterile packaging in any suitable state. Suitable states include, for example, a hydrated or dehydrated state. The graft devices can be dehydrated by any means known in the art (e.g., lyophilization or air dried). If a graft device of the present invention is stored in a dehydrated state, it is preferred that it retains all of its biological and mechanical properties (e.g., shape, density, flexibility, etc.) upon rehydration.

The materials and other properties of the packaging will be selected accordingly. For example, the package can include indicia to communicate the contents of the package to a person and/or a machine, computer, or other electronic device. Such indicia may include the dimensions of, the type of materials used to form, and/or the physical state of, the contents of the package. In certain embodiments, the graft device is packaged for sale with instructions for use. For example, in a particularly preferred embodiment, a medical product includes at least one graft device sealed within a sterile package, wherein the packaging can have visible indicia identifying the at least one graft device as having physical characteristics as disclosed herein, and/or can contain or otherwise be associated with printed materials identifying the contents as having such physical characteristics and including information concerning its use as a graft device. The packaging could also include visible indicia relating to the dimension of the at least graft device, and/or relating to the treatment site(s) for which the at least one graft device is configured.

Further, remodelable materials used in the invention may be manipulated at any stage during the medical graft product manufacturing process (e.g., before, during, or after a bonding or enriching step). Illustratively, a layer of material may be cut, trimmed, sterilized, and/or treated (e.g., brought into contact, impregnated, coated, etc.) with one or more desirable compositions, such as any of those previously disclosed herein, e.g., anticoagulants (e.g., heparin), growth factors or other desirable property modifiers. Also, any excess material can be trimmed at any suitable time within the manufacturing process, or even on-site during use of the medical graft product.

Also, it is advantageous in certain embodiments to perform any processing steps (e.g., drying, compressing, etc.) under relatively mild temperature exposure conditions that minimize deleterious effects upon components of the layers of remodelable material, for example, native collagen structures and potentially bioactive substances present in the ECM material layers. Thus, drying and other processing operations conducted with no or substantially no duration of exposure to temperatures above human body temperature or slightly higher, say, no higher than about 38° C., will preferably be used in some forms of the present invention. These include, for example, vacuum pressing operations at less than about 38° C., forced air drying at less than about 38° C., or either of these processes with no active heating— at about room temperature (about 25° C.) or with cooling. Relatively low temperature conditions also, of course, include lyophilization conditions.

Further, any exogenous growth factors or other bioactive substances incorporated into ECM material of the invention may be from the same species of animal from which the ECM material was derived (e.g. autologous or allogenic relative to the ECM material) or may be from a different species from the ECM material source (xenogenic relative to the ECM material). In certain embodiments, the ECM material is xenogenic relative to the patient receiving the graft, and any added exogenous material(s) are from the same species (e.g. autologous or allogenic) as the patient receiving the graft. Illustratively, human patients may be treated with xenogenic ECM materials (e.g. porcine-, bovine- or ovine-derived) that have been modified with exogenous human material(s) as described herein, those exogenous materials being naturally derived and/or recombinantly produced.

As used in the specification and claims, following long-standing patent law practice, the terms "a" and "an," when used in conjunction with the word "comprising" or "including" means one or more.

All publications and patent applications cited in this specification are herein incorporated by reference as if each individual publication or patent application were specifically and individually indicated to be incorporated by reference. Further, any theory, mechanism of operation, proof, or finding stated herein is meant to further enhance understanding of the present invention, and is not intended to limit the present invention in any way to such theory, mechanism of operation, proof, or finding. While the invention has been illustrated and described in detail in the drawings and foregoing description, the same is to be considered as illustrative and not restrictive in character, it being understood that only selected embodiments have been shown and described and that all equivalents, changes, and modifications that come within the spirit of the inventions as defined herein or by the following claims are desired to be protected.

What is claimed is:

1. A multilaminate medical graft product, comprising:
a first isolated tissue layer of remodelable collagenous extracellular matrix tissue material that promotes cellular invasion and ingrowth, said first tissue layer isolated from a biological tissue source;
a second isolated tissue layer of remodelable collagenous extracellular matrix tissue material that promotes cellular invasion and ingrowth, said second tissue layer isolated from a biological tissue source, wherein said second tissue layer is bonded to said first tissue layer;
a first bioactive component,
wherein said first isolated tissue layer is enriched with said first bioactive component relative to said second isolated tissue layer; and
a second bioactive component,
wherein said second isolated tissue layer is enriched with said second bioactive component relative to said first tissue layer; and wherein said first bioactive component and said second bioactive component are each selected from the group consisting of basic fibroblast growth factor (FGF-2), transforming growth factor-beta (TGF-β), epidermal growth factor (EGF), platelet derived growth factor (PDGF), cartilage derived growth factor (CDGF), vascular endothelial growth factor (VEGF) an anti-clotting agent, an antibiotic agent, an anti-inflammatory agent, a therapeutic protein, and an anti-proliferative agent.

2. The multilaminate medical graft product of claim 1, wherein at least one of said first tissue layer and said second tissue layer comprises submucosa, serosa, pericardium, dura mater, peritoneum, or dermal collagen.

3. The multilaminate medical graft product of claim 2, wherein both of said first tissue layer and said second tissue layer comprise submucosa.

4. The multilaminate medical graft product of claim 1, wherein said second tissue layer is essentially free of said first bioactive component.

5. The multilaminate medical graft product of claim 1, wherein said second tissue layer contains an amount of said first bioactive component, and the dry weight of said first bioactive component in said first tissue layer is at least about 10% greater than the dry weight of said first bioactive component in said second tissue layer.

6. The multilaminate medical graft product of claim 1, wherein said second tissue layer contains an amount of said first bioactive component, and the dry weight of said first bioactive component in said first tissue layer is at least about 20% greater than the dry weight of said first bioactive component in said second tissue layer.

7. The multilaminate medical graft product of claim 1, wherein said second tissue layer contains an amount of said first bioactive component, and the dry weight of said first bioactive component in said first tissue layer is at least two times greater than the dry weight of said first bioactive component in said second tissue layer.

8. The multilaminate medical graft product of claim 1 further comprising a third layer of remodelable extracellular matrix material bonded to at least one of said first tissue layer and said second tissue layer, said third remodelable extracellular matrix material layer being enriched with a second bioactive component relative to at least one of said first tissue layer and said second tissue layer.

9. The multilaminate medical graft product of claim 1 having a plurality of slits therein providing a mesh pattern, said mesh pattern being effective to provide an expansion ratio of at least about 1.2:1 to said graft product in a hydrated condition.

10. The multilaminate medical graft product of claim 1, wherein said first isolated tissue layer and said second isolated tissue layer each comprise at least 80% by weight collagen on a dry weight basis and retain uniaxial or multiaxial oriented fibers from the respective biological tissue sources from which said first tissue layer and said second tissue layer are isolated, and wherein said first isolated tissue layer includes at least about 3% retained non-collagenous solids from the biological tissue source from which said first tissue layer is isolated, the non-collagenous solids including an amount of said first bioactive component.

11. A method of preparing a multilaminate medical graft product, said method comprising the steps of:
providing a first isolated tissue layer of remodelable collagenous extracellular matrix tissue material that promotes cellular invasion and ingrowth, said first tissue layer isolated from a biological tissue source;
providing a second isolated tissue layer of remodelable collagenous extracellular matrix tissue material that promotes cellular invasion and ingrowth, said second tissue layer isolated from a biological tissue source, said first isolated tissue layer being enriched with a first bioactive component relative to said second isolated tissue layer, and said second isolated tissue layer being enriched with a second bioactive component relative to said first isolated tissue layer; and
bonding said first isolated tissue layer to said second isolated tissue layer.

12. The method of claim 11, wherein said bioactive component occurs natively in the biological tissue source from which said first tissue layer is isolated.

13. A medical product, comprising:
a multilaminate medical graft product enclosed within a sealed package, said graft product comprising:
a first isolated tissue layer of remodelable collagenous extracellular matrix tissue material that promotes cellular invasion and ingrowth, said first tissue layer isolated from a biological tissue source;
a second isolated tissue layer of remodelable extracellular matrix tissue material that promotes cellular invasion and ingrowth, said second tissue layer isolated from a biological tissue source, wherein said second tissue layer is bonded to said first tissue layer;
a first bioactive component,
wherein said first isolated tissue layer is enriched with said first bioactive component relative to said second isolated tissue layer; and
a second bioactive component,
wherein said second isolated tissue layer is enriched with said second bioactive component relative to said first isolated tissue layer.

14. A method of tissue grafting, comprising:
applying to tissue of a patient a multilaminate medical graft product comprising:
a first isolated tissue layer of remodelable collagenous extracellular matrix tissue material that promotes cellular invasion and ingrowth, said first tissue layer isolated from a biological tissue source;

a second isolated tissue layer of remodelable collagenous extracellular matrix tissue material that promotes cellular invasion and ingrowth, said second tissue layer isolated from a biological tissue source, wherein said second tissue layer is bonded to said first tissue layer;

a first bioactive component, wherein said first isolated tissue layer is enriched with said first bioactive component relative to said isolated tissue layer; and a second bioactive component, wherein said second isolated tissue layer is enriched in said second bioactive component relative to said first isolated tissue layer.

15. A method of treating an open cutaneous wound on a patient, comprising:

applying to the wound a multilaminate medical graft product, comprising:

a first isolated tissue layer of remodelable collagenous extracellular matrix tissue material that promotes cellular invasion and ingrowth, said first tissue layer isolated from a biological tissue source;

a second isolated tissue layer of remodelable collagenous extracellular matrix tissue material that promotes cellular invasion and ingrowth, said second tissue layer isolated from a biological tissue source, wherein said second tissue layer is bonded to said first tissue layer;

a first bioactive component, wherein said first isolated tissue layer is enriched with said first bioactive component relative to said second isolated tissue layer; and a second bioactive component, wherein said second isolated tissue layer is enriched with said second bioactive component relative to said first isolated tissue layer.

16. A multilayer medical graft product, comprising:

a first isolated tissue layer of remodelable collagenous extracellular matrix tissue material that promotes cellular invasion and ingrowth, said first isolated tissue layer isolated from a biological tissue source, said first isolated tissue layer comprising at least 80% by weight collagen on a dry weight basis and retaining uniaxial or multiaxial oriented fibers from said biological tissue source;

a second isolated tissue layer of remodelable collagenous extracellular matrix tissue material that promotes cellular invasion and ingrowth, said first isolated tissue layer isolated from a biological tissue source, said second isolated tissue layer comprising at least 80% by weight collagen on a dry weight basis and retaining uniaxial or multiaxial oriented fibers from said biological tissue source;

transforming growth factor beta, wherein said first isolated tissue layer is enriched with said transforming growth factor beta relative to said second isolated tissue layer.

17. The multilayer medical graft product of claim 16, wherein said first isolated tissue layer retains an amount of said transforming growth factor beta from the biological tissue source from which said first tissue layer is isolated.

18. The multilayer medical graft product of claim 17, wherein said second isolated tissue layer retains an amount of said transforming growth factor-beta from the biological tissue source from which said second tissue layer is isolated.

19. The multilayer medical graft product of claim 16, wherein said first tissue layer includes at least about 3% retained non-collagenous solids from the biological tissue source from which said first tissue layer is isolated, the non-collagenous solids including said first amount of said first bioactive component.

20. The multilayer medical graft product of claim 16, wherein said transforming growth factor beta includes an amount retained from the biological tissue source from which said first tissue layer is isolated and an amount that is exogenous.

21. The multilaminate medical graft product of claim 1, wherein said first bioactive component is vascular endothelial growth factor, and wherein said second bioactive component is platelet derived growth factor.

* * * * *